United States Patent
Olson et al.

(10) Patent No.: US 8,884,097 B1
(45) Date of Patent: Nov. 11, 2014

(54) METHOD TO CONDITION AN INVERTEBRATE TO DETECT A CONCENTRATION RANGE OF A CHEMICAL COMPOUND

(75) Inventors: Dawn M. Olson, Tifton, GA (US); Felix Wackers, Wray (GB); John-Erik Haugen, Aas (NO)

(73) Assignee: The United States of America as represented by the Secretary of Agriculture, Washington, DC (US)

(\*) Notice: Subject to any disclaimer, the term of this patent is extended or adjusted under 35 U.S.C. 154(b) by 199 days.

(21) Appl. No.: 13/590,272

(22) Filed: Aug. 21, 2012

Related U.S. Application Data

(60) Provisional application No. 61/527,168, filed on Aug. 25, 2011.

(51) Int. Cl.
*A01K 67/00* (2006.01)
*A01K 67/033* (2006.01)
*A01K 15/02* (2006.01)

(52) U.S. Cl.
USPC .......... 800/8; 119/705; 119/905; 800/3; 424/9.1

(58) Field of Classification Search
None
See application file for complete search history.

(56) References Cited

U.S. PATENT DOCUMENTS

2003/0148529 A1\* 8/2003 Lewis et al. .............. 436/63

OTHER PUBLICATIONS

Wright et al. "Different Thresholds for Detection and Discrimination of Odors in the Honey bee (*Apis mellifera*)." Chem. Senses(2004); 29: pp. 127-135.\*

Carcaud et al. "Odour aversion after olfactory conditioning of the sting extension reflex in honeybees." J Exp. Bio. (Mar. 2009); 212: pp. 620-626.\*

\* cited by examiner

*Primary Examiner* — Deborah Crouch
*Assistant Examiner* — Titilayo Moloye
(74) *Attorney, Agent, or Firm* — John Fado; Albert Y. Tsui; Lesley Shaw

(57) ABSTRACT

Described is a method of conditioning an invertebrate to detect a compound at and beyond a threshold range. In one embodiment the conditioned invertebrate is *Microplitis croceipes*. Compounds the invertebrate can detect include skatole and androstenone. An additional step includes selecting a compound and negatively conditioning the invertebrate at a concentration wherein the invertebrate will not respond to negatively conditioned compound concentration.

6 Claims, 11 Drawing Sheets

A

B

Skatole and Androstenone

METHOD TO CONDITION AN INVERTEBRATE TO DETECT A CONCENTRATION RANGE OF A CHEMICAL COMPOUND

CROSS-REFERENCE TO RELATED APPLICATION

This present application claims priority under 35 U.S.C. §119(e) to U.S. Provisional Ser. No. 61/527,168, which was filed on Aug. 25, 2011, and is hereby incorporated by reference.

FIELD OF THE INVENTION

The invention relates to the field of conditioning an invertebrate to respond to a compound of interest at a concentration range. More specifically, the invertebrate is conditioned to respond to a range of concentrations beyond a threshold concentration having been positively conditioned to respond to the threshold concentration or to a plurality of concentrations. In one embodiment of the invention, the conditioned invertebrate detects boar taint in a *Sus* sample. In particular, the invention provides a conditioned *Microplitis croceipes* that distinguishes a range of concentrations that include indole, skatole, and androstenone in a *Sus* sample.

BACKGROUND OF INVENTION

Invertebrates have experienced intense selection pressure for sensitive and effective ability to locate mates, food and hosts in nature. For example, *Microplitis croceipes* Cresson (Hymenoptera: Braconidae) are solitary insect endoparasitoids of the larvae of *Heliocoverpa zea* Boddie and *Heliothis virescens* Boddie and are able to learn and respond to volatile chemicals in amounts in at least the pico gram/s range (Wäckers et al., Journal of Food Science, Volume 76, 41-47, 2011). Such low detection thresholds are comparable to those of vertebrates (Smith et al., Annu. Rev. Entomol., Volume 39, 351-375, 1995; Stoddart, In: The Ecology of Vertebrate Olfaction, 58-62, 1980, Chapman and Hall, New York, N.Y.). The fact that invertebrates are able to learn allows them to be programmable. The breadth of invertebrate learning abilities has increasingly been studied and described (Fedodov, V P, J. of Evolutionary Biochemistry and Physiology, volume 45, 1-26, 2000; Willows et al., In. Invertebrate Learning. Plenum Press, New York, 1973-1975; Abramsom, C I, In. Invertebrate Learning, Washington D.C., American Psychological Assn., 1990; Zang, W., Environmental Monitoring and Assessment, volume 130, 415-422, 2007; Papaj et al., In. Insect Learning. Ecological and Evolutionary Perspectives. Chapman and Hall, 1993; Vet et al., In: Chemical Ecology of Insects 2, 65-101, 1995, Chapman and Hall, New York, N.Y.; Menzel et al., In. Biology of Learning: Report of the Dahlem Workshop on the Biology of Learning, 249-270, Springer-Verlag, Berlin, 1983).

One approach in detecting compounds is to utilize conditioned invertebrates to detect the presence of a compound. One such model invertebrate is the insect species, *Microplitis croceipes*, as disclosed in U.S. Pat. No. 6,919,202 and U.S. Pat. No. 7,607,338 and incorporated herein by reference. U.S. Pat. No. 6,919,202 discloses a method of training an organism to detect at least one chemical by repeated exposure of a biological resource in the presence of a target chemical. U.S. Pat. No. 7,607,338 discloses a similar method to detecting the presence of at least one chemical wherein a trained insect is utilized in conjunction with a portable handheld apparatus.

However U.S. Pat. Nos. 6,919,202 and 7,607,338 are limited in that the objective of the training is the detection of the conditioned chemical compound or blend of compounds, rather than the detection of a particular concentration. For the actual detection of particular concentrations, or ranges of concentrations (above or below a threshold), there is a need to further investigate conditioning methods in which the organism to be conditioned is conditioned at the threshold concentration or at a range of concentrations of a particular compound.

There is a crucial need to develop an invertebrate biosensor based on an organisms' ability to detect and report specific concentrations of targeted compounds. The detection of a compound of interest at and beyond a threshold concentration is particularly relevant in a number of applications, for example the monitoring of food quality, plant-, animal- and human-health. Although there are few studies of odor concentration learning in invertebrates, several studies of honeybees, *Apis mellifera* (Hymenoptera: Apidae) (Marfaing et al., J. Insect Physiol., volume 35, 949-955, 1989; Bhagavan and Smith, Physiol. Behav., volume 61, 107-117, 1996; Wright et al., Proc. R. Soc. B 271: 147-152, 2004; but see Pelz et al., J. Exp. Biol. 200: 837-847, 1997) found that learning and detection of odors is concentration dependent. Marfaing et al. (J. Insect Physiol., volume 35, 949-955, 1989) and Wright et al. (Proc. Royal Soc. B. volume 272, 2417-2422, 2005) also showed that concentration learning and detection of odors in the honeybee is compound dependent, and Wright et al. (J. Comp. Physiol. A 191: 105-114, 2005) further showed that learning and detection of compounds in mixtures depends on the concentration and the ratio (proportion) of the compounds in a mixture. Kaiser and De Jong (Animal Learning & Behavior 23: 17-21, 1995), found that the parasitoid *Leptopilina boulardi* (Hymenoptera: Figitidae) responds to absolute and relative concentrations of banana and strawberry odors in accordance with their conditioning concentration.

In one particular application, use of a conditioned invertebrate can detect a broad range of concentrations of a compound related to boar taint. Boar taint is an offensive odor or taste emanating from pork products. The boar taint is derived from non-castrated male pigs and the major chemicals responsible for boar taint are skatole and androstenone (Lundstrom K, et al., 2009, *Animal* 3:1497-1507). Skatole (3-methyl-indole) and androstenone (5α-androst-16-en-3-one) are fat soluble and accumulated in fat tissue of male pigs upon reaching sexual maturity. As such, if the concentration of skatole in adipose tissue of entire male pig exceeds 0.2 µg/g to 0.25 µg/g, consumers can perceive the tainted pork product. (Id.) For androstenone, consumers can perceive tainted pork products when androstenone is between 0.5 µg/g to 1.0 µg/g for the entire carcass. (Id.)

Methods to control for boar taint include castrating male pigs at an early age before reaching sexual maturity, selective breeding of only female pigs, selective breeding of pigs that are known to have low boar taint, or slaughtering pigs at an early age (approximately 6 months in age) so the skatole and androstenone do not accumulate in pre-adolescent adipose tissue.

However, the method of castrating male pigs have brought questions of animal welfare concerns. Specifically, in the European Union animal welfare concerns during the castration process has moved the EU to seek alternatives to castration. Furthermore, the EU has set a goal to end surgical castration of pigs in the future. Given that boar castration may be limited, there is a need to develop a low cost and rapid post-slaughtering methodology to detected boar taint.

There is a need to further investigate invertebrate ability to learn odor concentrations and whether the invertebrate response is compound dependent and incorporating those compound dependent responses to detect a range of compounds.

BRIEF SUMMARY OF THE INVENTION

Disclosed herein is a method of conditioning an invertebrate to detect a compound at and beyond a threshold range, the method comprising: (a) selecting an invertebrate to be conditioned, (b) selecting a compound to which the invertebrate selected to be conditioned will detect, (c) conditioning the invertebrate to respond to a threshold concentration of the selected compound, (d) conditioning the invertebrate to respond to a plurality of conditioning concentrations wherein each conditioning concentration is greater than the threshold concentration and each conditioning concentration is at a different concentration from each conditioning concentration, (e) repeating step (d) at least three times at each conditioning concentration, wherein the conditioned invertebrate responds to a range of concentrations of the selected compound at a range at the threshold and higher concentrations.

In another embodiment of the invention, the invertebrate trained is *Microplitis croceipes*. In a specific embodiment of the invention, the compound detected is skatole or androstenone. In another specific embodiment, the conditioned invertebrate detects skatole at a concentration range of about 0.1 µg/ml to about 100 µg/ml. In another specific embodiment, the conditioned invertebrate detects androstenone at a range of about 0.01 µg/ml to about 1 µg/ml.

In yet another embodiment of the invention, the method of conditioning an invertebrate to detect a compound at and beyond a threshold range further comprises negatively conditioning the invertebrate at a concentration wherein the invertebrate will not respond to the negatively conditioned compound concentration.

In another embodiment of the invention is the invertebrate conditioned to detect a plurality of compounds.

In a specific embodiment of the invention, the compound detected is indole. In yet another embodiment of the invention, an invertebrate is conditioned to detect indole at threshold conditioning concentration and negative trained to indole at a concentration of about one-hundred times greater than the threshold conditioning concentration.

BRIEF DESCRIPTION OF THE DRAWING

The present invention together with the above and other objects and advantages may best be understood from the following detailed description of the embodiment of the invention illustrated in the drawings, wherein:

In FIG. 1A females were conditioned to respond to 100 µg/ml of indole and exposed to 100 µg/ml and 1 µg/ml of indole. In FIG. 1B females conditioned to respond to 1 µg/ml of indole and exposed to 100 µg/ml and 1 µg/ml of indole.

In FIG. 3A conditioned females were exposed to 100 µg/ml, 10 µg/ml of skatole, and dichloromethane (DCM). In FIG. 3B conditioned females were exposed to 100 µg/ml, 1 mg/ml of skatole, and DCM.

In FIG. 4A conditioned females were exposed to 10 µg/ml, 1 µg/ml of skatole, and DCM. In FIG. 4B conditioned females were exposed to 10 µg/ml, 100 µg/ml of skatole, and DCM.

In FIG. 5A conditioned females were exposed to 1 µg/ml, 0.1 µg/ml of skatole, and DCM. In FIG. 5B conditioned females were exposed to 1 µg/ml, 10 µg/ml of skatole, and DCM.

In FIG. 6A conditioned females were exposed to 0.01 µg/ml and 0.1 µg/ml of androstenone. In FIG. 6B conditioned females were exposed to 0.01 µg/ml and 0.001 µg/ml of androstenone.

In FIG. 7A conditioned females were exposed to 0.1 µg/ml and 1 µg/ml of androstenone. In FIG. 7B conditioned females were exposed to 0.1 µg/ml and 0.01 µg/ml of androstenone.

In FIG. 8A conditioned females were exposed to 1 µg/ml and 0.1 µg/ml of androstenone. In FIG. 8B conditioned females were exposed to 1 µg/ml and 10 µg/ml of androstenone.

In FIG. 9A conditioned females were positively conditioned to respond to 0.900 µg/g of skatole and 5.450 µg/g of androstenone (=high) and negatively conditioned to 0.052 µg/g of skatole and 0.194 µg/g of androstenone (low). The females were then exposed to the positively and negatively conditioned concentrations. In FIG. 9B conditioned females were positively conditioned to respond to 0.900 µg/g of skatole and 5.450 µg/g of androstenone (=high) and negatively conditioned to 0.412 µg/g of skatole and 0.740 µg/g of androstenone (=med). The females were then exposed to the positively and negatively conditioned concentrations.

In FIG. 10 conditioned females were positively conditioned to respond to 0.050 µg/g of skatole and 0.194 µg/g of androstenone (=low) and negatively conditioned to 0.90 µg/g of skatole and 5.450 µg/g of androstenone (=high). The females were then exposed to the positively and negatively conditioned concentrations.

In FIG. 11A females were positively conditioned to 100 µg/ml and negatively conditioned to 1 µg/ml of skatole and exposed to skatole at 1 µg/ml, 10 µg/ml, 100 µg/ml and 1 mg/ml. In FIG. 11B females were positively conditioned to 100 µg/ml and 1 mg/ml skatole and exposed to 1 µg/ml, 10 µg/ml, 100 µg/ml and 1 mg/ml of skatole.

DETAILED DESCRIPTION OF THE INVENTION

Definitions

Figure 1:
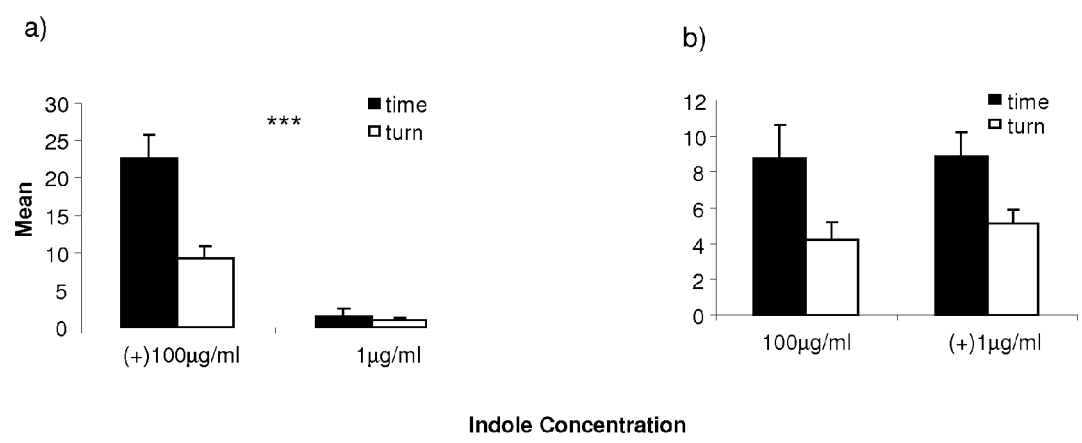
FIGS. 1A and 1B are graphs depicting mean plus standard error of the mean (SEM) time and turns of female *Microplitis croceipes* conditioned to respond to a concentration of indole.

As used in the specification and claims, the singular form "a", "an" and "the" include plural references unless the context clearly dictates otherwise. For example, a conditioned *Microplitis croceipes* includes the use of a plurality of *Microplitis croceipes* unless indicated otherwise.

The term "threshold concentration" as used herein refers to the lowest end of the compound concentration in a sample that requires identification.

The term "positive conditioning" refers to rewarding an invertebrate that responds to a compound at a selected concentration so that the invertebrate associates the compound at the selected concentration with a positive reinforcement. In the example of *Microplitis croceipes*, sucrose-water is an example of positive conditioning reward that creates a nexus with the insect responses to desirable concentrations of a compound. With positive conditioning, a plurality of concentrations of a compound can be used to condition the invertebrate.

The term "negative conditioning" refers to conditioning an invertebrate not to respond to a selected compound concentration so that the invertebrate associates the compound at the selected concentration with a negative reinforcement. In the example of the *Microplitis croceipes*, water is an example of negative reinforcement that creates a nexus with the insect responses to undesirable compound concentrations. With negative conditioning, a plurality of concentrations of a compound can be used to condition the invertebrate.

The term "boar taint" refers to undesirable taste or smell in pork meat. Chemical contributing to boar taint include but are not limited to the compounds 3-methyl-indole, 5α-androst-16-en-3-one, and indole.

The approach in using stingless wasps as biosensors is to place conditioned wasps in a chemical detection system. This system uses conditioned parasitic wasps held in small cartridges. Sample air is pumped into the device through a small inlet (Rains, Utley & Lewis, 2006). Wasps walk freely within the cartridge and can respond to the sample air with specific behaviors. (Wäckers et al., Entomologia Experimentalis et Applicata, Vol. 103, Number 2, 2002, pg. 135-138)

A video camera integrated in the bio sensor captures insect behavior and a behavioral analysis program graphs and identifies the insect's response. In Utley et al., Trans ASABE, volume 50, 1843-1849, 2007, describes a method and apparatus utilizing wasps as a model insect to capture responses to stimuli and the reference is incorporated herein by reference.

In a preferred embodiment of the invention, conditioned insects are used in conjunction with a biosensor having a portable computer vision system to detect a range of chemical odors. One such embodiment of the computer vision system is described in U.S. Pat. No. 7,607,338 and incorporated herein by reference.

The present invention separates a very specific behavior from its biological context for use as a reporting device, called a response behavior. This response behavior is defined for purposes of the present invention as any behavior the organism usually displays when in close proximity to a biological resource such as, for example, food, mate, prey, or host. This response behavior can be isolated from the organism's natural behavioral context and used with any chemical cue using the conditioning method as set forth in U.S. patent application Ser. No. 09/826,146 and herein incorporated by reference in its entirety. The method of the '146 application quickly programs the organisms in at least about 1 minute and brings the organisms to report conditioned odors, especially odors not related to the biology of the organism, with high accuracy under a range of environmental conditions. The conditioned organisms can pick out a single chemical from a chemical blend after being conditioned to that chemical. Knowledge of the chemical nature of the programmed odors is not necessary.

For purposes of the present invention, invertebrates include, for example, Arthropods, including but not limited to wasps, bees, moths, butterflies, beetles, true bugs (e.g. assassin bugs); and arachnids, for example, including but not limited to spiders, mites, ticks, and scorpions; Crustaceans, for example, including but not limited to crayfish, lobster, and crabs; and mollusks, for example, including but not limited to snails, slugs, squids, and clams.

The parasitic wasp, *Microplitis croceipes*, is used as a model organism, to show conditioned organisms in a system for chemical detection. *Microplitis croceipes* (Cresson) (Hymenoptera: Braconidae) is a solitary larval parasitoid of *Heliothis* and *Helicoverpa* species (Hymenoptera: Noctuidae). Adult females forage for food and hosts according to their physiological needs and females may use learned odors to locate both resources. Thus, females with experience on a plant-host complex or on host frass (faeces) are attracted to the odor of the plant-host complex and to host frass odor. Naive females antennating frass link it with an odor with a nonvolatile recognition kairomone found in frass that reinforces associative learning. In a similar fashion, naive females that are feeding on nectar or sugar water link the associated odor to the food resource. In this manner, wasps learn odors associated with the presence of hosts or food and subsequently use these odors as cues while foraging for more hosts or adult food. Wasps are readily conditioned to fly, coil, head-stick or antennate in response to odors associated with a host or food source. In the following food-associated examples, the time spent antennating and turning around a hole where odor is emitted (region of interest), is recorded.

To demonstrate and evaluate the ability of *Microplitis croceipes* to show specific conditioned responses to the three individual boar taint compounds, classical conditioning paradigms were used allowing pairing of the individual odor (conditioned stimulus) with sugar feeding (unconditioned reward). Using an established bioassay (Wäckers et al., 2002; Rains et al. 2004) evaluation of whether conditioned wasps would exhibit specific food-seeking behaviors when presented with either the individual odors or a blend of all three odors.

EXAMPLE 1

Female Wasps Conditioned to Indole at 100 µl/ml and 1 µl/ml

Female wasps were conditioned to a 30 µl solution of indole (Spectrum Chemical MFG CORP., Gardena, Calif.) dissolved in dichloromethane at either 100 µg/ml or 1 µg/ml. The solvent was allowed to evaporate for one min before the assay. The conditioning arena consisted of a 9 cm d, 1.5 cm h metal ring covered with aluminum foil that was placed inside a glass petri dish (10 cm d and 1 cm h) containing the compound-laden filter paper (2.5 cm d). A small (4 mm$^2$) piece of filter paper laden with the sugar water (1 molar sucrose solution) was placed at the center of the metal ring covered with aluminum foil. A total of 9 holes (ca 1 mm d) were punctured around the tissue paper so that diffusing volatiles could be perceived as they fed on the sugar water. Wasps were allowed to feed for 10 s three times with 30 s between feedings. All conditioning and testing was done under a chemical fume hood. The conditioning arena was replaced with fresh materials after every 5 females (ca 10-15 min). Females were placed in a Plexiglas cage with water for 2 hrs before testing. A total of 20 females were conditioned per day over 2 days.

All test solutions were allowed to evaporate for 1 minute before being presented to the wasps. The test arena was the same as the conditioning arena except that only a single (ca 1 mm d) hole was punctured at the center of the aluminum foil covered metal ring. Wasps were placed close to the hole using a transfer vial. Measured were food-specific behaviors (Wäckers et al., 2002) which included intense substrate antennation with frequent tight turning, a distinct lowering of the head for food searching and attempts to enter the hole. Responses parameters included a recordation of both the number of turns and overall duration of the food searching. Each female was presented a single odor concentration. A total of 20 females (10 to high and 10 to low concentrations) were tested per day over 2 days. Kruskal-Wallis non-parametric ANOVA was used to test the effect of concentration on wasp responses (StatSoft, Inc. 2003). As disclosed in FIG. 1A, wasps conditioned to 100 µg/ml responded to the conditioned concentration, but the wasp did not respond to a ten-fold decrease from the conditioned concentration of 1 µg/ml of indole. Wasp conditioned to 1 µg/ml of indole responded to the conditioned concentration of 1 µg/ml and to a ten-fold increase from the fold increase from the conditioned indole concentration as disclosed in FIG. 1B).

EXAMPLE 2

Figure 2:
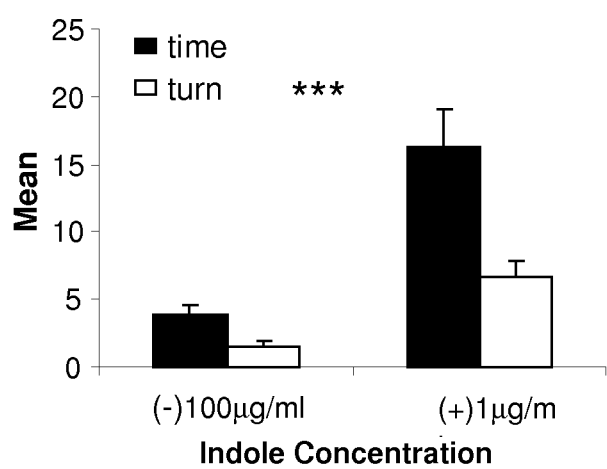
FIG. 2 is a graph depicting mean plus SEM time and turns of female *Microplitis croceipes* conditioned to respond to 1 µg/ml of indole and negatively conditioned to a 100 µg/ml of indole.

Positive Food Conditioning to Indole at 100 µg/ml and 1 µg/ml while Negative Conditioning to Indole at 100 µg/ml The arena and procedure for testing were as described in Example 1. However, the wasps were conditioned via positive food conditioning of sugar-water to indole at 1 µg/ml. Additionally, the same wasp was also negatively food conditioned to 100 µg/ml of indole with water. Each female was test with a single indole concentration at either 100 µg/ml of indole or at 1 µg/ml. A total of 20 females (10 to high and 10 to low concentrations) were tested per day over 2 days. As depicted in FIG. 2, the wasps responded to the conditioned concentration but did not respond to the negatively conditioned concentration. This is in contrast to FIG. 1B where wasps lacking in a negative conditioning to 1 µg/ml did not distinguish that concentration of indole.

EXAMPLE 3

Conditioning to Individual Concentrations of Skatole

Figure 3:
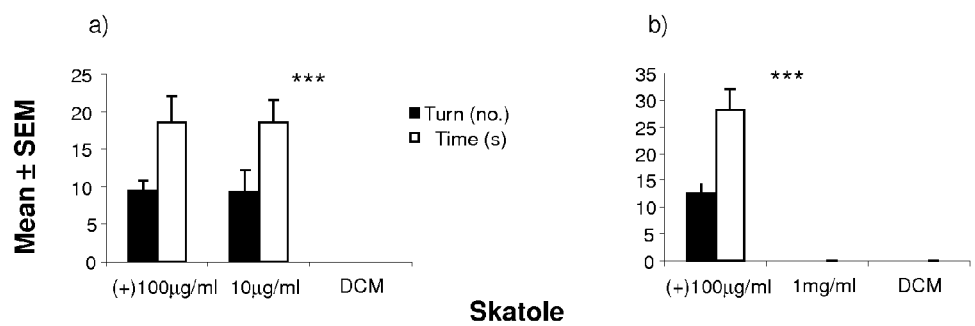
FIGS. 3A and 3B are graphs depicting mean plus SEM time and turns of female *Microplitis croceipes* conditioned to respond to 100 µg/ml of skatole.

The arena and procedure for testing were as described in Example 1. However, the wasps were conditioned via positive food conditioning of sugar-water to 30 µl of conditioning solution of skatole dissolved in dichloromethane at either 0.001 µg/ml, 0.01 µg/ml, 0.1 µg/ml, 1 µg/ml, 10 µg/ml, or 100 µg/ml. A 1 molar sucrose solution was used as the unconditioned stimulus (reward).
Conditioned to 100 µg/ml of Skatole
  Wasps conditioned to 100 µg/ml skatole and tested to detected skatole at 100 µg/ml, 10 µg/ml and DCM (control) responded to both skatole concentrations (FIG. 3A), but when tested to skatole at 100 µg/ml, 1 mg/ml and DCL, they only responded to the conditioning concentration (FIG. 3B).

Figure 4:
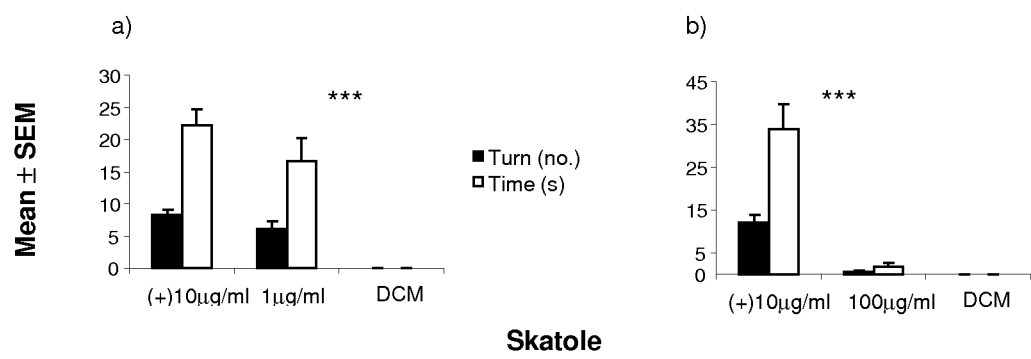
FIGS. 4A and 4B are graphs depicting mean plus SEM time and turns of female *Microplitis croceipes* conditioned to respond to 10 µg/ml of skatole.
Figure 5:
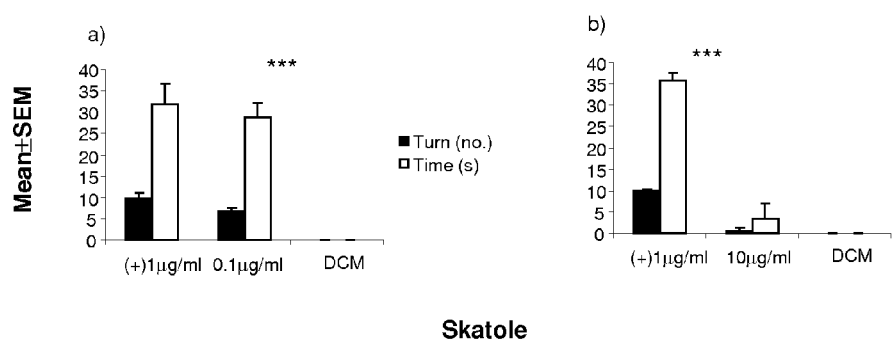
FIGS. 5A and 5B are graphs depicting mean plus SEM time and turns of female *Microplitis croceipes* conditioned to respond to 1 µg/ml of skatole.

Conditioned to 10 µg/ml of Skatole
  Wasps conditioned to 10 µg/ml skatole and tested to skatole at 10 µg/ml, 1 µg/ml and DCM (control) responded to both skatole concentrations (FIG. 4A), but when tested to skatole at 10 µg/ml, 100 µg/ml and DCL, they only responded to the conditioning concentration (FIG. 4B).
Conditioned to 1 µg/ml of Skatole
  Wasps conditioned to 1 µg/ml skatole and tested to skatole at 1 µg/ml, 0.1 µg/ml and DCM (control) responded to both concentrations (FIG. 5A), but when tested to skatole at 1 µg/ml, 10 µg/ml and DCM only responded to the conditioning concentration (FIG. 5B).
  Wasps conditioned to skatole at 0.1 µg/ml showed no responses to 0.1 µg/ml, 1 µg/ml and DCL, suggesting that they do not learn this low of a concentration of skatole, however, they are able to detect it as shown in FIG. 5A.

EXAMPLE 4

Conditioning to Individual Concentrations of Androstenone

Figure 6:
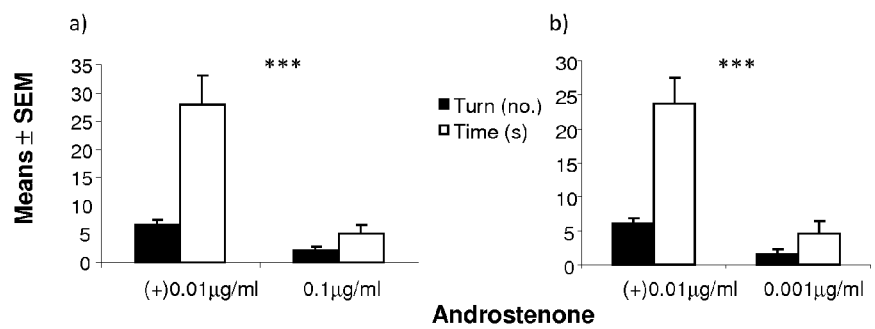
FIGS. 6A and 6B are graphs depicting mean plus SEM time and turns of female *Microplitis croceipes* conditioned to respond to 0.01 µg/ml of androstenone.
Figure 7:
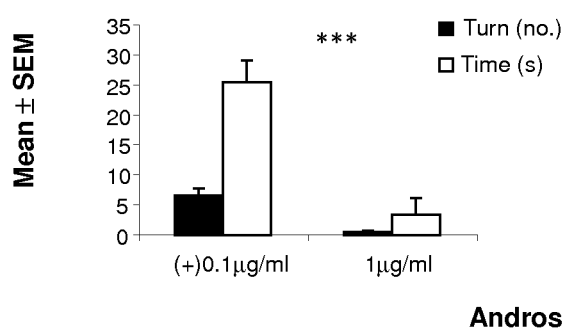
FIGS. 7A and 7B are graphs depicting mean plus SEM time and turns of female *Microplitis croceipes* conditioned to respond to 0.1 µg/ml of androstenone.
Figure 7:
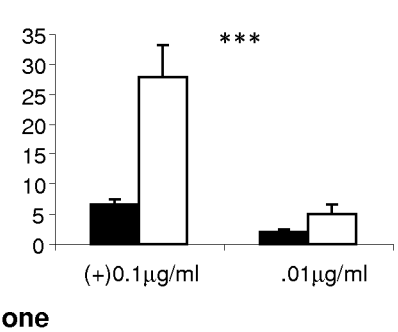
Figure 8:
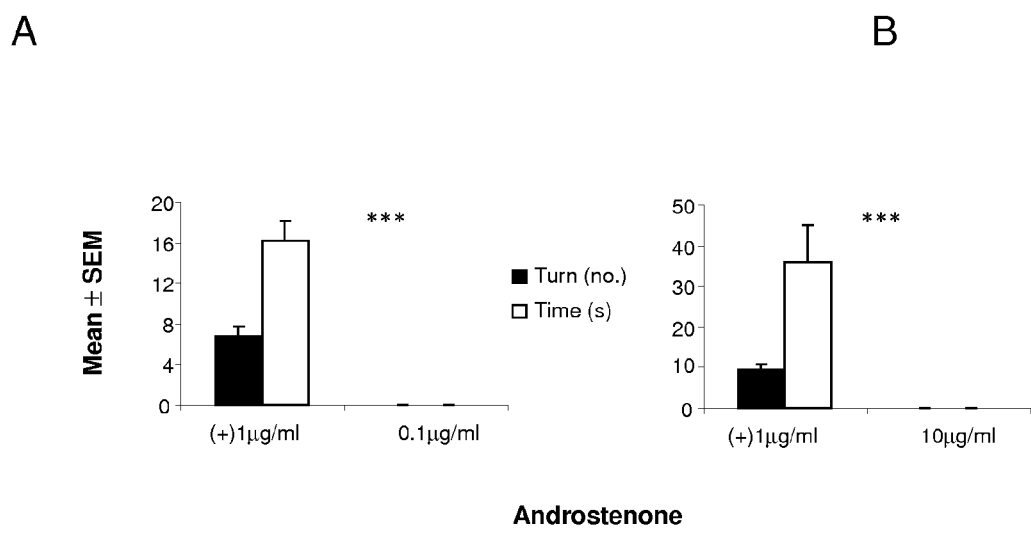
FIGS. 8A and 8B are graphs depicting mean plus SEM time and turns of female *Microplitis croceipes* conditioned to respond to 1 µg/ml of androstenone.

Conditioned to 0.01 µg/ml of Androstenone
  The arena and procedure for testing were as described in Example 3. Wasps conditioned to 0.01 µg/ml androstenone and tested to 0.01 µg/ml, 0.1 µg/ml responded to the conditioning concentration but not to the higher and lower concentrations of 0.1 µg/ml and 0.001 µg/ml of androstenone, respectively. (FIGS. 6A & 6A).
Conditioned to 0.01 µg/ml of Androstenone
  Wasps conditioned to 0.1 µg/ml of androstenone and tested to 0.1 µg/ml, 1 µg/ml and 0.01 µg/ml only responded to the conditioning concentration (FIGS. 7A & 7B).
Conditioned to 1 µg/ml of Androstenone
  Wasps conditioned to 1 µg/ml of androstenone and tested to 1 µg/ml, 0.1 µg/ml and 10 µg/ml only responded to the conditioning concentration (FIGS. 8A & 8B).
  Wasps conditioned to 10 µg/ml of androstenone and tested to 10 µg/ml and 1 µg/ml did not respond to either concentration.

EXAMPLE 5

Wasp Positively Conditioned to Two Concentrations of Skatole

Figure 11:
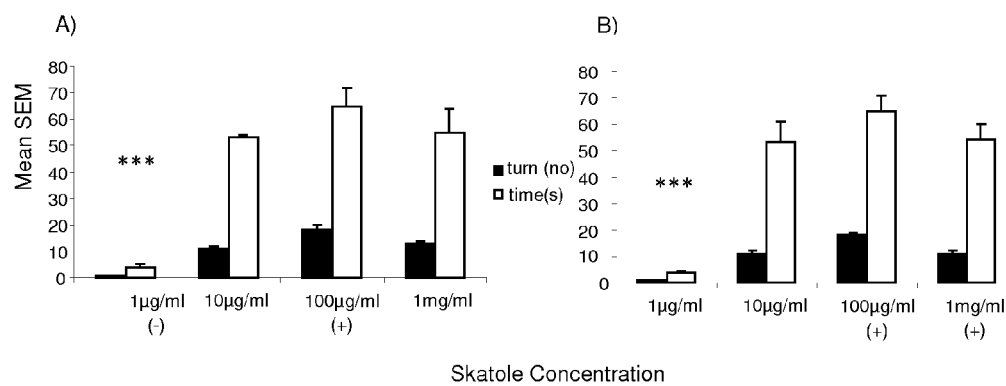
FIG. 11 is a graph depicting mean plus SEM time and turns of female *Microplitis croceipes* positively and negatively conditioned to various concentrations of skatole.

The arena and procedure for testing were as described in Example 1. Wasps positively conditioned (given sucrose-water) to skatole at 100 µg/ml and 1000 µg/ml and tested to skatole at 1 µg/ml, 10 µg/ml, 100 µg/ml and 1000 µg/ml responded to both of the conditioning concentrations as well as to the 10 µg/ml concentration (FIG. 11). This is in contrast to FIG. 3B wherein conditioning to a single concentration of 100 µg/ml didn't yield a response to 10 µg/ml.

EXAMPLE 6

Test of Boar Fat Samples

In addition, boar fat samples were used for conditioning and testing, containing respectively low levels of skatole (0.050 µg/g) and androstenone (0.200 µg/g), medium levels of skatole (0.412 µg/g) and androstenone (0.412 µg/g) and high levels of skatole (0.900 µg/g) and androstenone (5.450 µg/g).
  Wasps were conditioned to 30 µl of conditioning solution consisting of either androstenone, or skatole dissolved in dichloromethane at either 0.001 µg/ml, 0.01 µg/ml, 0.1 µg/ml, 1 µg/ml, 10 µg/ml, or 100 µg/ml. A 1 molar sucrose solution was used as the unconditioned stimulus (reward).

Response of wasps to solvent (control), and conditioning odor at conditioning concentration or at 10-fold lower, or 10-fold higher concentration. Initial results indicated that the wasps conditioned to high or low concentrations of skatole and androstenone in boar fat responded to both concentrations regardless of the concentration used in conditioning. Therefore, both a negative and positive reinforcement method is used to increase discrimination between the chemical concentrations.

Figure 9:
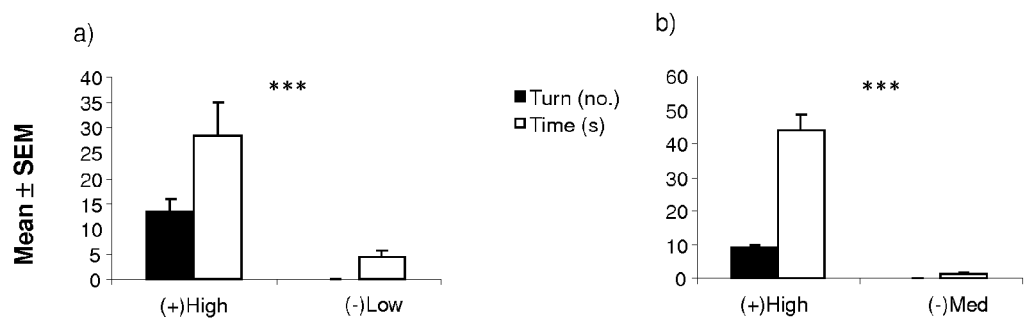
FIGS. 9A and 9B are graphs depicting mean plus SEM time and turns of female *Microplitis croceipes* conditioned to respond to concentrations of skatole and androstenone combined in boar fat.

Wasps were positively conditioned (sugar-water) to either high or low concentrations of androstenone or skatole in boar fat and negatively conditioned (water only) to either low, high or medium concentrations of androstenone or skatole in boar fat. A 1 molar sucrose solution was used as the unconditioned stimulus (reward). Wasps positively conditioned (given sucrose-water) to boar fat containing low concentrations of indole, skatole and androstenone, and negatively conditioned (water only) to boar fat containing high concentrations of indole, skatole and androstenone responded to the boar fat containing the conditioning concentration (FIG. 9).

The results from the single odor experiment show that individual wasps can be conditioned to respond reliably to indole and skatole as individual volatiles, with the former evoking a more prolonged response. The conditioned response is highly specific, witnessed by the fact that conditioned wasps do not respond to the solvent (DCM) or a non-conditioned floral odor (ocimene). Conditioned responses to androstenone, on the other hand are weak, both in terms of percentage responding and in terms of duration of the response.

Figure 10:
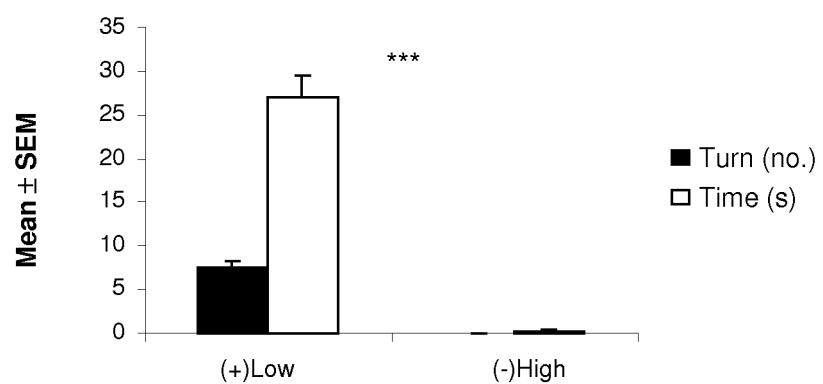
FIG. 10 is a graph depicting mean plus SEM time and turns of female *Microplitis croceipes* conditioned to respond to concentrations of skatole and androstenone combined in boar fat.

Wasps were positively conditioned (given sucrose-water) to boar fat at room temperature (25° C.) containing low concentrations of skatole (0.050 µg/g) and androstenone (0.200 µg/g), and negatively conditioned (water only) to boar fat containing high concentrations of skatole (0.900 µg/g) and androstenone (5.450 µg/g) responded to the boar fat containing the conditioning concentration (FIG. 10).

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the invention has been described with reference to details of the illustrated embodiment, these details are not intended to limit the scope of the invention as defined in the appended claims.

The embodiment of the invention in which exclusive property or privilege is claimed is defined as follows:

1. A method of conditioning an invertebrate to detect a compound at and beyond a threshold range, the method comprising:
    (a) selecting a *Microplitis croceipes* to be conditioned,
    (b) selecting a compound to which the *Microplitis croceipes* selected to be conditioned will detect,
    (c) conditioning the *Microplitis croceipes* to respond to a threshold concentration of the selected compound,
    (d) conditioning the *Microplitis croceipes* sequentially to respond to a plurality of positive conditioning concentrations wherein each positive conditioning concentration is greater than the threshold concentration and each conditioning concentration is different from any previously learned positive conditioning concentration,
    (e) repeating step (d) at least three times at each conditioning concentration, wherein the conditioned *Microplitis croceipes* responds to a range of concentration of the selected compound at a range between the threshold concentration and highest conditioning concentration.

2. The method of claim 1 wherein the compound is skatole or androstenone.

3. The method of claim 2 wherein the *Microplitis croceipes* detects skatole at a concentration range of about 0.1 µg/ml to about 100 µg/ml.

4. The method of claim 2 wherein the invertebrate *Microplitis croceipes* detects androstenone at a concentration range of about 0.01 µg/ml to about 1 µg/ml.

5. The method of claim 1 further comprising selecting indole as the compound of (b) and negatively conditioning the *Microplitis croceipes* at a concentration wherein the *Microplitis croceipes* will not respond to a negatively conditioned compound concentration.

6. The method of claim 5 wherein the negative conditioning concentration is about one-hundred times greater than the threshold conditioning concentration.

* * * * *